United States Patent [19]
Field

[11] Patent Number: 5,599,184
[45] Date of Patent: Feb. 4, 1997

[54] PROTECTIVE SYSTEM FOR DENTAL DRILL UNITS

[76] Inventor: Roger C. Field, Postfach 950169, 81517 Munich, Germany

[21] Appl. No.: 338,109

[22] Filed: Nov. 9, 1994

[30] Foreign Application Priority Data

Nov. 16, 1993 [DE] Germany ............................ 9317549 U

[51] Int. Cl.⁶ .................................................. A61C 1/05
[52] U.S. Cl. ............................................................ 433/115
[58] Field of Search ..................................... 433/104, 115, 433/116, 82

[56] References Cited

U.S. PATENT DOCUMENTS 2,041,077  5/1936  Lininger ................................. 433/116
3,098,299  7/1963  Page ...................................... 433/115
4,218,216  8/1980  Sugai et al. ........................... 433/104
4,310,309  1/1982  Favonio ................................. 433/104

Primary Examiner—Cary E. O'Connor

[57] ABSTRACT

A protective system for dentist chill units including a protective element and a sealing substance around the drill to prevent the entrance of undesirable matter such as the HIV (AIDS) virus into the handpiece holding the drill, which may, when the drill is replaced by another drill, infect the next patient, the system including an optional device including at least one valve for preventing undesirable matter such as the HIV virus from remaining in the water system after possible entry through one or more water nozzles in the handpiece, once the water is pumped out and possibly replaced by disinfectant, and then again with cooling water.

16 Claims, 3 Drawing Sheets

PROTECTIVE SYSTEM FOR DENTAL DRILL UNITS

The invention is a mechanical system for preventing the entry of fluid containing medically undesirable elements such as the HIV virus and hepatitis A and B into the handpiece which holds a dentist's drill, and as an option, for preventing same from entering the water system, possibly infecting the next patient.

Dentist drills usually turn at a very high speed, often about 400,000 RPM. They may be powered by compressed air acting on a turbine, which needs to turn the turbine and the drill at very high RPM to provide enough power to the drill to drill into teeth. It is common practice to use water to cool the drill bit. When saliva and blood mix with this water, a bridge for undesirable elements such as the HIV (AIDS) virus is formed by the liquid between the tip of the drill and the area around the portion of the handpiece head holding the drill. It is possible for this mixture of saliva, water and possibly blood to enter the handpiece with, e.g., the HIV virus. When the drill is removed to be disinfected and a new drill inserted for another patient, a bridge between the new drill tip and the handpiece may be formed again by water and/or saliva and possibly blood. The virus inside the handpiece may now descend via the fluid connecting the handpiece to the tip of the drill and enter the new patient's bloodstream via any bleeding which occurs in his mouth.

It is common practice to sterilize each handpiece used for several minutes at high temperature, e.g. approximately 130 degrees centigrade in an autoclave or other device for heat sterilization. This practice entails owning several handpieces and is thought to quickly deteriorate the quality of internal components. This practice is encouraged in developed countries, but is in fact often reduced to one or two sterilizations per day, benefiting only the next patient. There is the additional possibility of the HIV virus and other elements entering the water system via the water opening or openings near the drill, which act as nozzles for directing coolant water onto the drill. The bridge formed by the aforementioned liquid between the drill tip and the handpiece may extend to these openings.

It is the purpose of the invention to provide a simple mechanical alternative to heat sterilization to prevent undesirable elements such as the HIV virus from entering the dentist's handpiece or the water supply or both.

A device described as a protective element is positioned around the drill bit, onto the housing, or integrated into the housing of the handpiece or may be part of the handpiece head housing. This protective element includes any device placed concentrically around the drill bit, whether partially attached to the drill bit, e.g., such as a center section within an outside element, or an outside element surrounding the drill bit itself. The protective element may also be a sleeve around the attach point for the drill, usually a long sleeve attached within the lower bearing and extending upwards. In this embodiment, oil or grease, for example, preferably synthetic oil, is placed in the opening of the drill bit and the attach point sleeve and the gap between the attach point sleeve and the sleeve of the protective element. Oil or grease or other substance is preferably placed on part of the drill bit when it is inserted into the sleeve, in one embodiment of the invention. The protective element is sealed by grease or oil, for example, silicone oil, or some other agent which may be continually or occasionally introduced into or placed in the protective element, or a part of the protective element attached to the drill, or another part of the protective element, or even the drill, may have grease or other substance for sealing. Ferro fluid may be used (e.g. with a magnetized part or parts).

Compressed air used to turn the turbine or cool the motor of an electric drill should preferably be diverted to prevent it escaping around the drill bit, as this would push out the oil, unless oil or grease or other substance is introduced to seal the gaps when the turbine or motor is turned off and air is not pushed out in the vicinity of the drill bit. In one embodiment, the turbine and attach point sleeve may be retracted to apply oil to the protective element.

An optional additional device may be incorporated, if desired, into the system for preventing, e.g. the HIV virus, from entering the water system.

The protective element may be large enough in outside dimension to surround any openings such as the ball bearing or other type of bearing supporting part of the drill bit, as well as where the drill bit is attached to the handpiece. The protective element can therefore encapsulate these openings. One or more seals such as "o" rings may be used to seal the protective element against the protective housing. An agent such as a lubricating agent, preferably oil or grease or vaseline, for example (preferably non-toxic) is used to seal the protective element when the drill is turning or when it is not turning, to prevent water from entering through the protective element to the drill attachment point and its bearing. At least one hole or nozzle for water for cooling, preferably with compressed air, should be placed outside the protective element, if cooling water is used. The protective element may be rigidly incorporated into or attached to the handpiece housing or it may float to accommodate side pressure on the drill bit to prevent inner friction. One or more "o" rings may be used to seal the protective element to the housing. The handpiece has at least one opening for cooling water mixed with air, or at least one separate air hole or nozzle.

One or more valves may, as an option, be used to seal the water hose or handpiece when the system is not activated. A switch may be positioned on the floor, which is actuated by the dentist for turning on the drill. When the switch is off and the water is not pushed out of the handpiece under pressure, these valves close to block entry of the virus into the water system.

After a patient, the valve furthest from the handpiece remains closed, the water pumped out and the water hose filled with disinfectant for a period of time. The valve may also be in the handpiece, in one embodiment. The disinfectant is pumped out of the hose and/or the handpiece and water is again pumped through, once the valves are opened, and out of the handpiece. The drill bit is changed and disinfected. The area of the protective element may be wiped prior to or after removal of the drill bit. The whole protective element may be removed and disinfected or sterilized and substituted with another one if this is deemed necessary.

It is possible to control the grease or other matter in the protective element by introducing grease or other matter in the protective element from a container, preferably attached to the handpiece. Grease may be pushed out of the container by a piston which may, for example, be moved by air pressure from the compressed air frequently used to turn the turbine and frequently mixed with the cooling water, e.g. through a separate nozzle. Grease may also be placed on a sleeve attached around the drill, e.g. from a dispenser separate from the handpiece, before the drill is inserted into the handpiece.

If a sleeve is attached to the drill bit, or made in one piece with it, one or more grooves may be located around the sleeve to retain the grease or other matter used to provide a seal. A sleeve attached to the drill bit may be made e.g. of Teflon. A sleeve fitting around the inner sleeve preferably with very little clearance would retain the oil or grease, and if a grease supply is provided, as described above, grease or other matter would be supplied to the protective element if the grease were used up or pushed out of the protective element. It is possible for one or more holes to be provided through the outside sleeve of the protective element to enable grease or other matter used to be replaced with fresh grease or other substance for sealing. It is also possible to have the one ore more recessed grooves inside the outer sleeve, or in both sleeves. In another embodiment, it is possible to have no grooves at all. It is possible to have a simple sleeve around the drill bit itself, which may be filled with grease or other matter, which may be fed from a container. This sleeve may also have one or more grooves for retaining grease. A dispenser may be used for automatically putting grease on part of the protective element. A sleeve on the protective element may have inner walls diverging downwards, to accommodate side pressure on the drill bit.

Current handpieces with turbines or electric motors force air out around the drill bit. Turbines also suck air in with contaminated matter when idling to a stop. It is desirable to divert air under the turbine, for example, by tube along the handpiece or within it to prevent this.

The handpiece head may possibly have one or more openings apart from the bearing and drill attach point (not the water nozzle or nozzles or air hole or holes for cooling water) which need to be encapsulated by the protective element, depending on the design of the handpiece. The outside of the handpiece may be wiped with disinfectant between patients. The drill bit release button should be watertight, if one is provided.

It is possible to design the relationship between the inner and outer sleeves in several ways to best retain tile grease in the protective element. The protective element may also be one or more ball bearings attached to the drill bit and mounted watertight (preferably with at least one "o" ring) to the handpiece head.

Many variations of this invention are possible.

Four preferred embodiments of the invention are described in detail.

Figure 1:
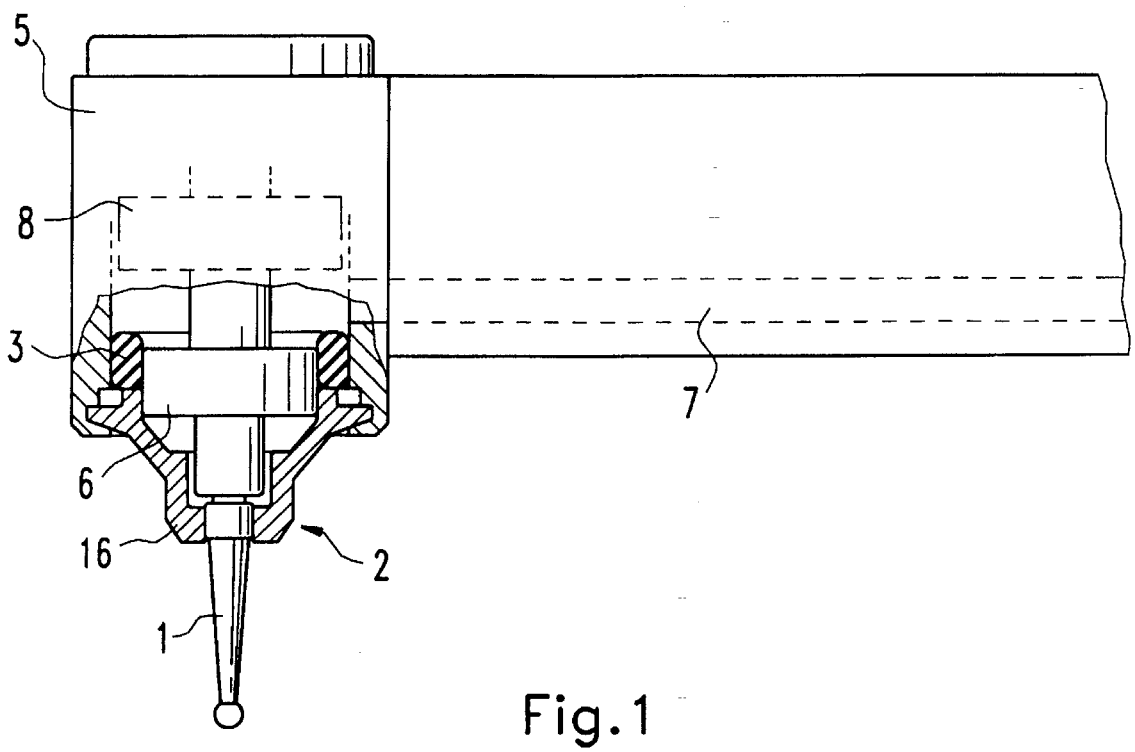
FIG. 1 shows a partly cut open side view of a handpiece with a drill bit surrounded by a sleeve.

FIG. 1 shows a partially cut open side view of handpiece 5. Drill bit 1 is attached to handpiece 5 and is located inside protective element 2. Protective element 2 which comprises an outside sleeve 16 concentrically located around drill bit 1 is attached to handpiece housing 5 by a bayonet mount (not shown) and abuts against rubber "o" ring 3 and around the base of ball bearing 6, so that any lateral bending of drill bit i will not result in friction from drill bit 1 against outside sleeve 16, outside sleeve 16 being able to move with any slight lateral movement of ball bearing 6. Channel 7 under and to one side of turbine 8 allows air to escape without leaving the area or drill bit 1, and prevents air from being sucked in around drill bit 1 during idling of turbine 8.

Figure 2:
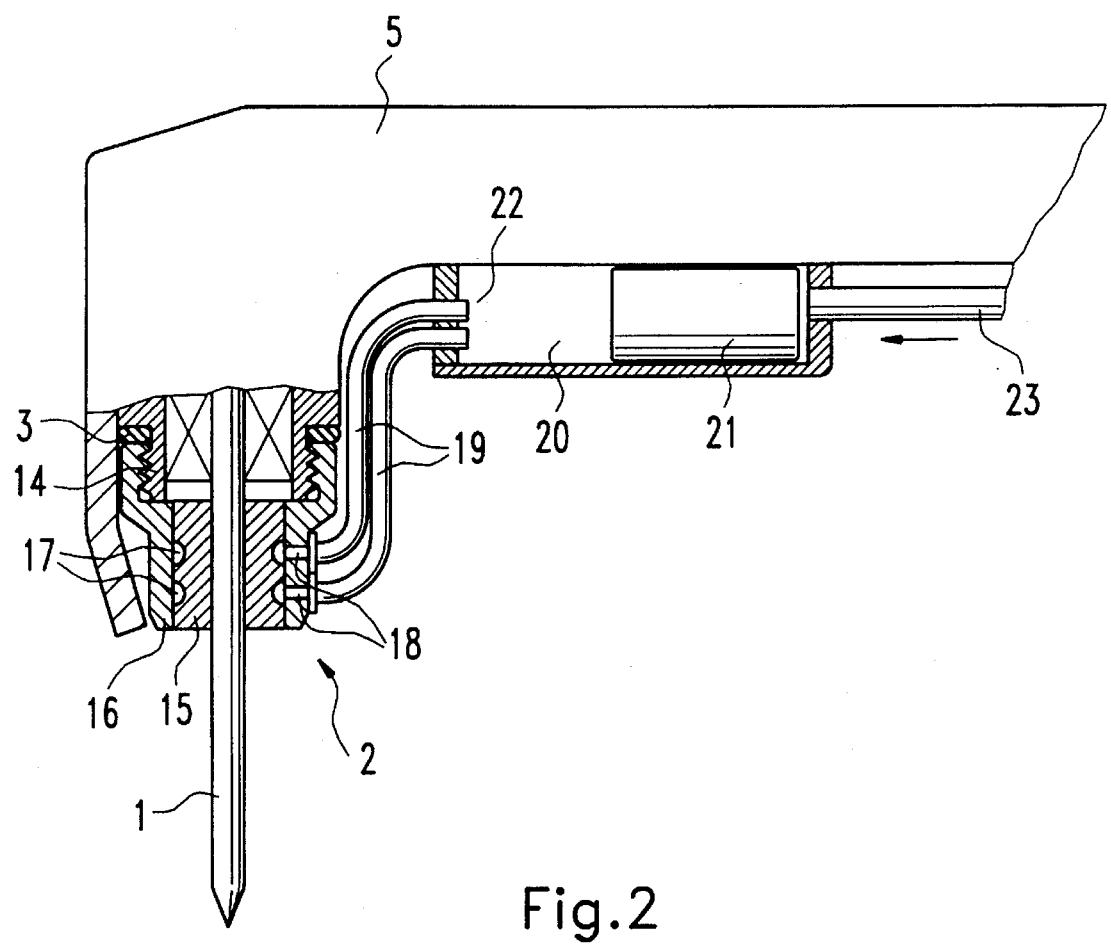
FIG. 2 shows a partly cut open side view of a handpiece with a drill bit attached to a sleeve, surrounded by a second sleeve.

FIG. 2 shows a similar embodiment to that shown in FIG. 1. Inside sleeve 15 is attached to drill bit 1 and is water tight. Inside sleeve 15 is concentrically mounted when drill bit 1 is inserted into handpiece 5, within outside sleeve 16. Inside sleeve 15 of protective element 2 has two grooves 17 concentrically located in its outside diameter. Outside sleeve 16 has two holes 18 drilled into its side. Two tubes 19 are attached to two holes 18 and are attached to container 20. Compressed air forced through tube 23 acts against piston 21 located concentrically within container 20 which forces grease through two tubes 19 through holes 18 into grooves 17 located in the outside diameter of inside sleeve 15. Grooves 17 contain grease, sealing the gap between inside sleeve 15 and outside sleeve 16. Outside sleeve 16 is attached to handpiece housing 5 via threads 14 which have enough play to allow inside sleeve 15 and outside sleeve 16 to move laterally should lateral pressure against drill bit 1 cause it to bend slightly during use. "o" ring 3 seals outside sleeve 16 of bearing 2 against handpiece housing 5 and allows it to move with drill bit 1 should it bend with lateral pressure against teeth, and then straighten, while remaining watertight.

Figure 3:
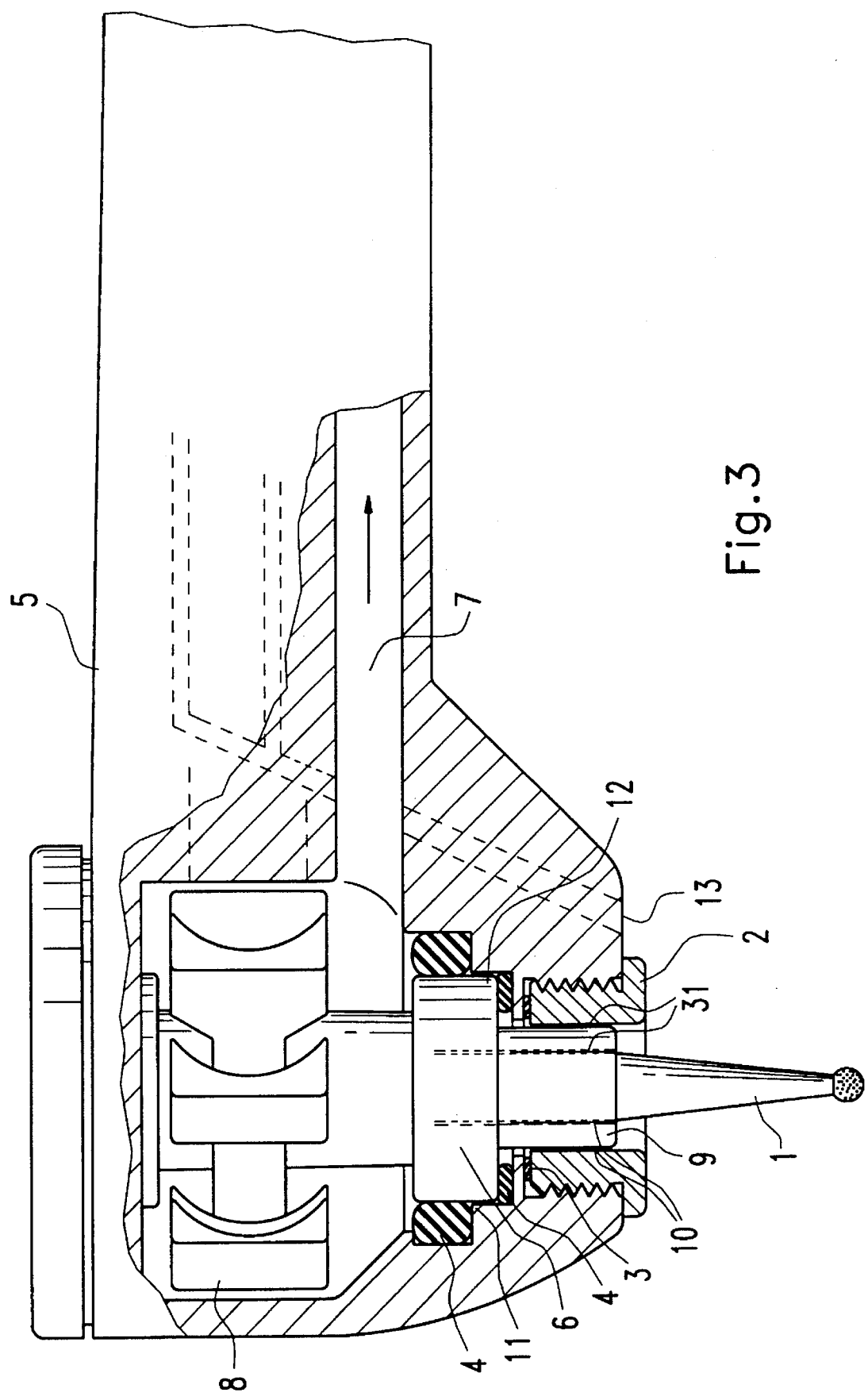
FIG. 3 shows a partly cut open side view of a handpiece with a drill bit attached.

FIG. 3 shows a partly cut olden side view of a handpiece with a drill bit attached. Drill bit 1 is attached to sleeve 9 within ball bearing 6. A film of synthetic oil 31 which has been placed on drill bit 1 before insertion into sleeve 9 forms a seal between drill bit 1 and sleeve 9. Protective element 2 is a sleeve made of nylon threaded into handpiece 5 and abutting against "o" ring 3 which seals protective element 2 against handpiece 5. A film of synthetic oil 31 which has been placed on protective element 2 seals gap 10 between protective element 2 and sleeve 9. "o" ring 4 between handpiece 5 and ball bearing 6 supports ball bearing 6 and prevent high speed noise from ball bearing 6 to transfer to handpiece 5. Shoulder 12 which does not rotate, of ball bearing 6 is closely positioned to shoulder 11 of handpiece 5 to abut against it if undue side pressure is exerted on drill bit 1, to prevent rubbing of sleeve 9 on protective element 2. Protective element 2 is made of nylon to prevent damage, over-heating or excessive noise in case sleeve 9 should touch protective element 2 during rotation. Channel 7 is located under turbine 8 and allows compress air not fed back through handpiece 5 radially from turbine 8 to exit handpiece 5 behind and clear of operator's hand, thereby preventing compressed air from exiting handpiece 5 through the vicinity of drill bit 1, and preventing air from being sucked into handpiece 1 during idling of turbine 8 after compressed air has been turned off. Water nozzle 13 is positioned outside the location of protective element 2.

Figure 4:
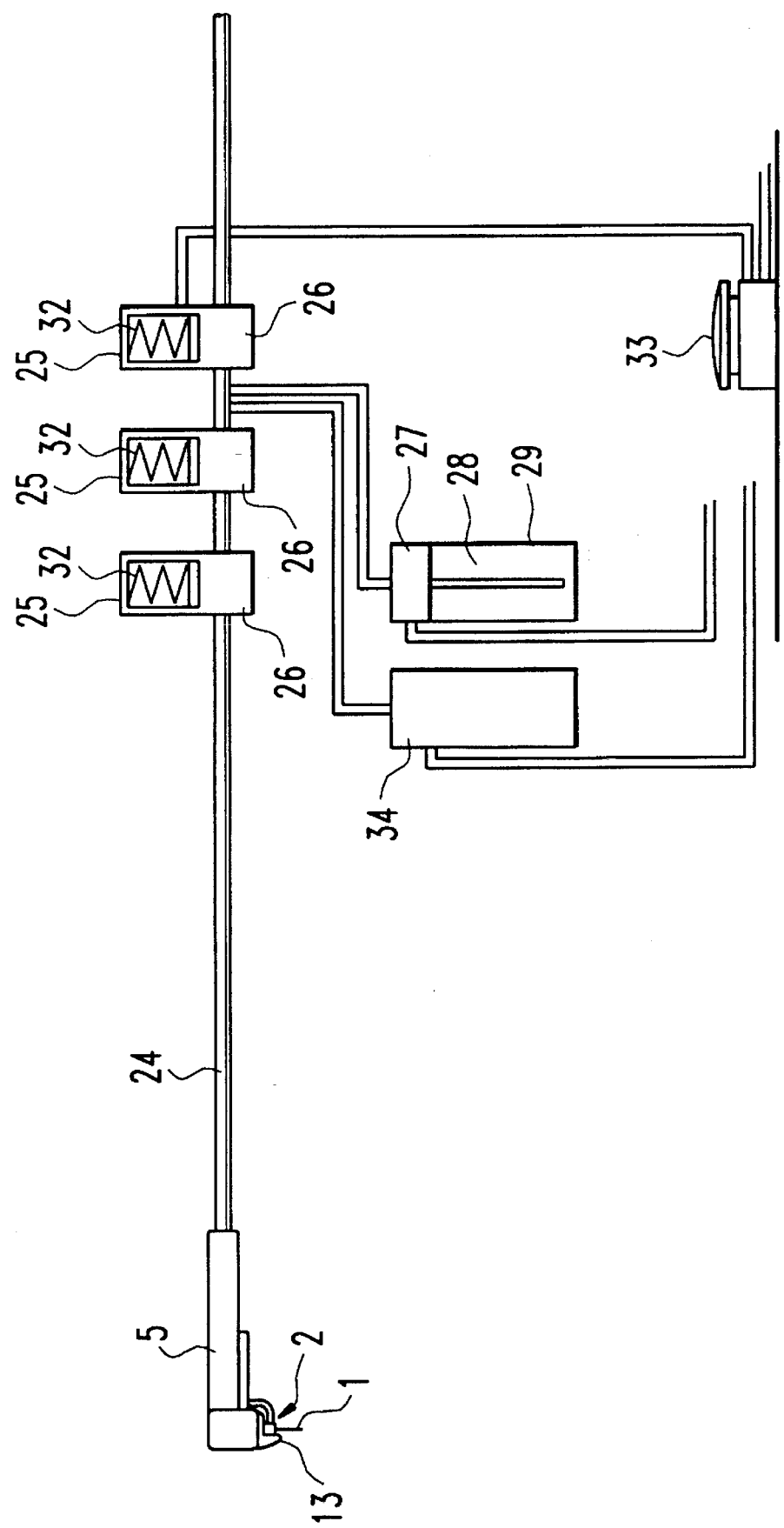
FIG. 4 shows a side view of a handpiece attached to a water hose attached to three precision valves.

FIG. 4 shows a side view of handpiece housing 5 attached by tube 24 to valves 25. Three precision valves 25 are provided to prevent undesirable matter such as the HIV virus from gaining access to the water supply after the three valves. When valves 25 are open, water is forced through tube 24 out of handpiece housing 5 which has two water nozzles 13 for cooling drill bit 1. Valves 25 are electrically connected to switch 33 mounted on the floor. Solenoids 26 open valves 25 when current is introduced to them when drill 1 is tuned on, allowing water to be pumped through tube 24. When switch 33 is activated to the "off" position, the valves close under spring pressure from springs 32. Before treating another patient, two valves 25 closest to handpiece 5 are manually opened and water is pumped out of tube 24 by pump 34. Disinfectant 28 within bottle 29 attached to pump 27 attached to assembly of valves 25, is pumped through two valves 25 and tube 24 until water has been replaced by disinfectant 28. Pump 27 is then turned off and disinfectant is allowed to remain in two valve assembly 25 and tube 24 for a period of time. Disinfectant 28 is pumped out of two-valve assembly 25, two valves 25 being mechanically held open, until disinfectant is pumped out hose 24 and two valves 25. Two valves 25 are then allowed to close under spring pressure. Drill bit 1 may be turned on electrically by switch 33 allowing valves 25 to open with no risk of undesirable matter such as the HIV virus contaminating the water supply and water may be pumped to handpiece 5.

I claim:

1. A protective system against entrance of undesirable matter such as the HIV virus into a dentist's drilling apparatus, said drilling apparatus including a handpiece with a removeable drill bit having an outside circumference, at least one bearing with a sleeve for attaching said drill bit to said handpiece, said sleeve having an inside and an outside circumference, said bearing having an outside circumference, said handpiece having at least one opening for cooling water, in the vicinity of said sleeve for attaching said drill bit, said handpiece being provided with compressed air, the improvement comprising at least one substance and at least one protective element for the prevention of undesirable matter such as the HIV virus from entering said drilling apparatus by including the interaction of at least one substance and at least one protective element for sealing against entrance of said undesirable matter between said outside circumference of said removeable drill bit and said inside circumference of said sleeve for attaching said drill bit and preventing the entrance of said undesirable matter into said bearing, into the vicinity of said bearing and around said circumference of said bearing, into said handpiece, said compressed air being channelled so as to allow said at least one substance to seal, said at least one opening for cooling water being located outside the sealing area of said substance and said protective element, to provide cooling for said drill bit.

2. Protective system as in claim 1 wherein said protective element encircles said sleeve for attaching said drill bit, said substance for sealing being placed between said protective element and said outside circumference of said sleeve for attaching said drill bit and said substance for sealing being placed between said sleeve for attaching said drill bit and said drill bit for sealing against said undesirable matter.

3. Protective system as in claim 1 wherein said at least one protective element is a sleeve concentrically located around said removeable drill bit.

4. Protective system as in claim 1 wherein said at least one protective element is concentrically located on said removeable drill bit, concentrically located within an outer sleeve when said removeable drill bit is attached to said handpiece.

5. Protective system as in claim 4 wherein said at least one protective element concentrically located on said removeable drill bit has at least one groove located concentrically around it.

6. Protective system as in claim 1 wherein said at least one protective element has at least one groove concentrically located within it.

7. Protective system as in claim 1 wherein said substance for sealing said at least one protective element is a lubricant.

8. Protective system as in claim 1 wherein said substance for sealing said at least one protective element is oil.

9. Protective system as in claim 1 wherein said substance for sealing said at least one protective element is kept in a container.

10. Protective system as in claim 1 wherein said substance for sealing said at least one protective element is kept in a container located on said handpiece.

11. Protective system as in claim 1 wherein said substance for sealing said at least one protective element is automatically fed from said container into said protective element.

12. Protective system as in claim 1 wherein said at least one protective element is a ball bearing.

13. Protective system as in claim 1 wherein moving air in said handpiece is diverted from leaving the vicinity of said drill bit to prevent said air from pushing said substance for sealing out of said handpiece and for preventing a turbine from sucking air into said handpiece and for preventing said turbine from sucking air into said handpiece when idling to a stop.

14. Protective system as in claim 1 wherein air leaves said handpiece in the vicinity of said drill bit and said substance is introduced for sealing in the vicinity of said drill bit when said system is turned off and said air is no longer pushed out of said vicinity of said drill bit.

15. Protective system as in claim 1 wherein said substance for sealing is mixed with disinfectant.

16. Protective system as in claim 1 wherein said at least one nozzle for cooling water is connected via said handpiece to a water supply by at least one hose, said hose being provided with at least one valve to prevent undesirable matter such as said HIV virus from entering said hose and said water supply, said at least one valve closing when said removeable drill bit is turned off and said cooling water is stationary, said cooling water being pumped out of said hose and replaced by new water after optional replacement of said stationary cooling water with disinfectant.

\* \* \* \* \*